United States Patent [19]

Schroeppel

[11] Patent Number: 5,571,144
[45] Date of Patent: Nov. 5, 1996

[54] METHOD OF VERIFYING CAPTURE OF THE ATRIUM BY A CARDIAC STIMULATOR

[75] Inventor: Edward A. Schroeppel, Lake Jackson, Tex.

[73] Assignee: Intermedics, Inc., Angleton, Tex.

[21] Appl. No.: 574,240

[22] Filed: Dec. 18, 1995

[51] Int. Cl.$^6$ .................................................. A61N 1/37
[52] U.S. Cl. ............................................. 607/28; 607/26
[58] Field of Search ............................... 607/9, 11, 26–28

[56] References Cited

U.S. PATENT DOCUMENTS

| | | | |
|---|---|---|---|
| 4,686,988 | 8/1987 | Sholder | 607/28 |
| 4,858,610 | 8/1989 | Callaghan | 607/28 |
| 5,431,693 | 7/1995 | Schroeppel | 607/28 |
| 5,443,485 | 8/1995 | Housworth et al. | 607/28 |

*Primary Examiner*—William E. Kamm
*Assistant Examiner*—George R. Evanisko
*Attorney, Agent, or Firm*—Richard L. Robinson

[57] ABSTRACT

A method of verifying whether an atrium of the heart has been captured by an atrial cardiac stimulation pulse. An atrial signal is sensed via an electrode located in the atrium during a period of time from before delivery of the stimulation pulse to after delivery of the stimulation pulse. The sensed signal is analyzed by detecting whether a P-wave occurred prior to delivery of the cardiac stimulation pulse such that stimulation pulse would have been delivered within a refractory period. If a P-wave did not occur, the slope of the sensed waveform signal is determined within a selected interval of time beginning at a selected time after the time of delivery of the stimulation pulse. A capture status signal is generated that indicates non-capture, if a P-wave was detected, or capture, if a P-wave component was not detected and the determined slope of the sensed waveform signal surpasses a pre-selected slope threshold demarcating capture from non-capture.

16 Claims, 7 Drawing Sheets

5,571,144

1

METHOD OF VERIFYING CAPTURE OF THE ATRIUM BY A CARDIAC STIMULATOR

BACKGROUND OF THE INVENTION

1. Field of the Invention

The present invention relates generally to cardiac pacing using an implantable cardiac stimulator, and more particularly to verification of capture of the atrium of the heart following application of an electrical stimulating pulse by the cardiac stimulator.

2. Background Information

An implantable cardiac stimulator, specifically a pacemaker, "captures" the heart by delivering an electrical pulse via an electrode to the myocardium of a selected chamber during an interval in the cardiac cycle in which the cardiac tissue is excitable. The electrical pulse causes depolarization of cardiac cells and a consequent contraction of the chamber, provided that the energy of the pacing pulse as delivered to the myocardium exceeds a threshold value.

It is desirable to adjust the cardiac stimulator so that the pulse energy delivered to the myocardium is at the lowest level that will reliably capture the chamber. Such a level assures therapeutic efficacy while maximizing the life of the implanted battery. Because the threshold for capture varies from one implantation to another, and can change over time, it is also desirable that the pulse energy delivered by the cardiac stimulator to the myocardium be adjustable during and subsequent to implantation. Adjustment can be effected manually from time to time through use of an external programmer that communicates with the implanted pacemaker. It would be desirable, however, to provide a cardiac stimulator that adjusts the pulse energy automatically and dynamically in response to changes in the capture threshold.

Changes in capture threshold can be detected by monitoring the efficacy of stimulating pulses at a given energy level. If capture does not occur at a particular stimulation energy level which previously was adequate to effect capture, then it can be surmised that the capture threshold has increased and that the stimulation energy level should be increased. On the other hand, if capture occurs consistently at a particular stimulation level over a relatively large number of successive stimulation cycles, it is possible that the stimulation threshold has decreased and that stimulation energy is being delivered at a level higher than necessary. This can be verified by lowering the stimulation energy level and monitoring for loss of capture at the new energy level.

For automatic and dynamic adjustment of the stimulation energy level to be successful, it is necessary for the implantable cardiac stimulator to be able to verify that capture has occurred. Verification of capture in the ventricle has been accomplished by detecting a characteristic electrical potential in the heart evoked by the stimulating pulse. If capture has not occurred, there will be no characteristic evoked potential to detect. It follows that each time a stimulating pulse is delivered to the ventricle, the heart can be monitored during an appropriate period of time thereafter to detect the presence of the evoked potential, and thereby verify capture. In practice, however, reliable detection of the evoked potential of the ventricle is not a simple matter. This is because the evoked potential is small in amplitude relative to the residual polarization charge on the electrode resulting from the stimulation pulse. The residual charge decays exponentially but tends to dominate the evoked potential for several hundreds of milliseconds thereafter. Detection of the evoked potential of the atrium is even more difficult, as the amplitude of the atrial evoked potential is quite small and difficult to discriminate from noise, other cardiac signals, and the residual polarization charge on the electrode.

It would be desirable to provide a method for analyzing cardiac signals, for use in an implantable cardiac stimulator, that permits verification of capture of the atrium in the presence of a residual charge from a preceding stimulation pulse and in the presence of other signals. This and other desirable goals are met by the present invention.

SUMMARY OF THE INVENTION

According to one aspect of the invention, a method is provided for discriminating between capture and non-capture electrogram signal morphologies that are sensed in the atrium following delivery of a stimulation pulse to the atrium by a cardiac stimulator. The method involves detecting whether an intrinsic P-wave has occurred prior to the time of delivery of the atrial stimulating pulse, and determining the slope of the sensed atrial electrogram within a selected time interval beginning at a time following delivery of the atrial stimulating pulse. If no P-wave has been detected prior to the atrial stimulating pulse and the slope of the sensed electrogram surpasses a pre-selected slope threshold, as measured between two time-spaced sampled amplitudes of the sensed electrogram, then capture of the atrium is deemed to have occurred. Otherwise, a non-capture is presumed.

It is an object of the present invention to provide an improved method for distinguishing non-capture and capture waveform morphologies as sensed by an intracardiac atrial electrode following delivery of a cardiac stimulating pulse to the atrium.

Other objects and advantages of the present invention will be apparent from the following description of a preferred embodiment made with reference to the drawings.

DETAILED DESCRIPTION OF THE PREFERRED EMBODIMENT

Figure 1:
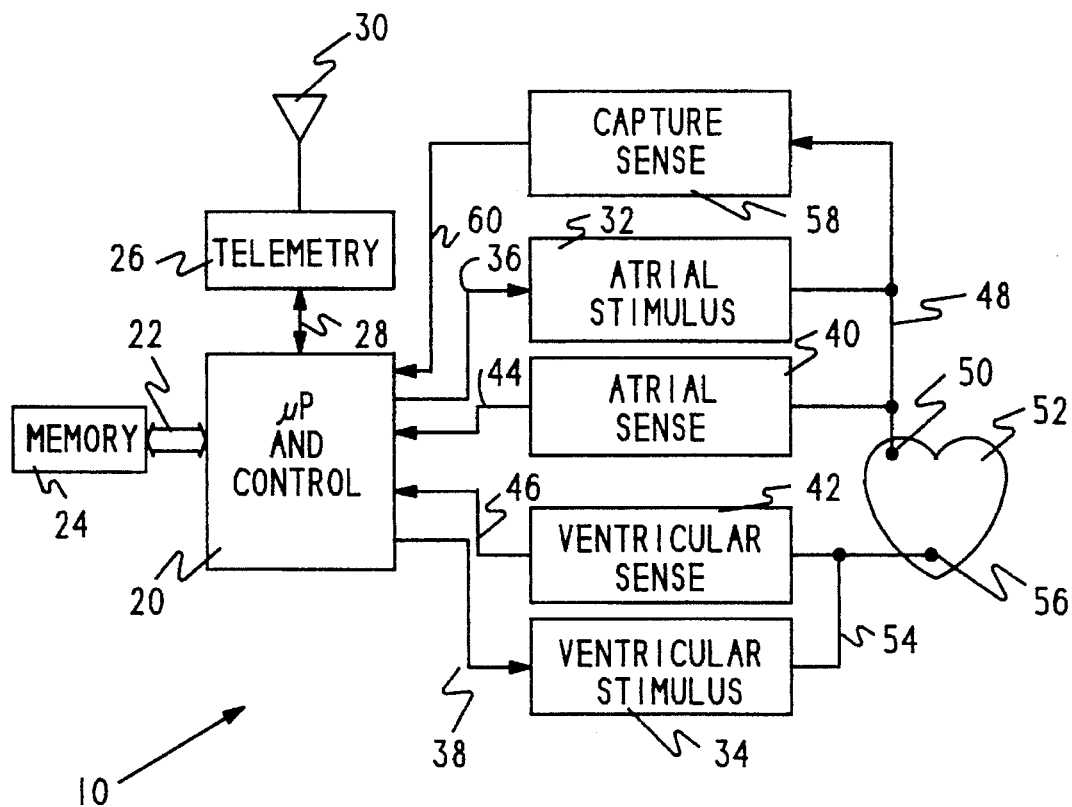
FIG. 1 is a block diagram of the preferred embodiment of a cardiac stimulator for practicing the method of the present invention.

Referring in particular to FIG. 1, there is illustrated a block diagram of a cardiac stimulator, or pacemaker, 10 with which the method of the present invention can be practiced. A microprocessor and control circuit 20 preferably provides pacemaker control and means for processing digital signals. Microprocessor 20 has input/output ports connected in a conventional manner via bi-directional bus 22 to memory 24. Memory 24 preferably includes both ROM and RAM, and stores the pacemaker operating routine and various programmable parameters and variables.

Microprocessor 20 preferably also has an input/output port connected to a telemetry interface 26 by line 28. The pacemaker when implanted is thus able to receive pacing control parameters and variables from a transmitter of an external programmer and send data to a receiver of the external programmer if desired. Telemetry communication is preferably effected by transmission and reception, via antenna 30, of electromagnetic radiation modulated in accordance with the data to be communicated.

Microprocessor 20 also has output ports connected to inputs of an atrial stimulus pulse generator 32 and a ventricular stimulus pulse generator 34 by control lines 36 and 38, respectively. Microprocessor 20 sends pulse parameter data, such as amplitude and width, as well as enable/disable and pulse initiation codes to the generators 32 and 34 on the respective control lines 36 and 38.

Microprocessor 20 also has input ports connected to outputs of an atrial sense amplifier 40 and a ventricular sense amplifier 42 by lines 44 and 46, respectively. The atrial and ventricular sense amplifiers 40 and 42 detect P-waves and R-waves respectively. The input of the atrial sense amplifier 40 and the output of the atrial stimulus pulse generator 32 are connected to a first conductor 48 which is connected via a conventional atrial lead to a pacing/sensing electrode 50 preferably lodged within the right atrial chamber of the heart 52.

The input of the ventricular sense amplifier 42 and the output of the ventricular stimulus pulse generator 34 are connected to a second conductor 54 which is connected via a conventional ventricular lead to a pacing/sensing electrode 56 preferably lodged within the right ventricular chamber of the heart 52.

The conductors 48 and 54 conduct the stimulus pulses generated by the atrial and ventricular stimulus pulse generators 32 and 34, respectively, to the pacing/sensing electrodes 50 and 56. The pacing/sensing electrodes 50 and 56 and corresponding conductors 48 and 54 also conduct sensed cardiac electrical signals in the right atrium and right ventricle to the atrial and ventricular sense amplifiers 40 and 42, respectively.

An atrial capture sense signal processor 58 has an input connected to conductor 48, and an output connected via line 60 to an input port of microprocessor 20. A signal sensed in the atrium by electrode 50 is conducted via conductor 48 to capture sense signal processor 58, where the sensed signal is processed in a manner described further below. The processed signal from capture sense signal processor 58 is conducted via line 60 to microprocessor 20 where the signal undergoes further processing and analysis in accordance with a method described below.

The present invention contemplates verifying capture of the atrium by sensing via an electrode placed in the atrium a waveform signal that is, among other things, indicative of the effect of a stimulating pulse delivered in the atrium. A significant advantage of the present invention is that the same electrode that is used to deliver the stimulating pulse can also be used for verifying capture. This allows use of unipolar pacing between the lead tip and the pacemaker housing without requiring a separate ring electrode for capture verification. Alternatively, bipolar sensing between the lead tip and a ring electrode can be used together with unipolar pacing. This has the advantage of minimizing the sensing of far-field R-waves. In addition, bipolar pacing can be used together with bipolar sensing. The method is suitable for single chamber pacing/sensing, but may also be used with a dual-chamber device. An advantage of the latter arrangement is that detection of the R-wave in the ventricle can be used to identify farfield R-waves sensed in the atrium.

Figure 2:
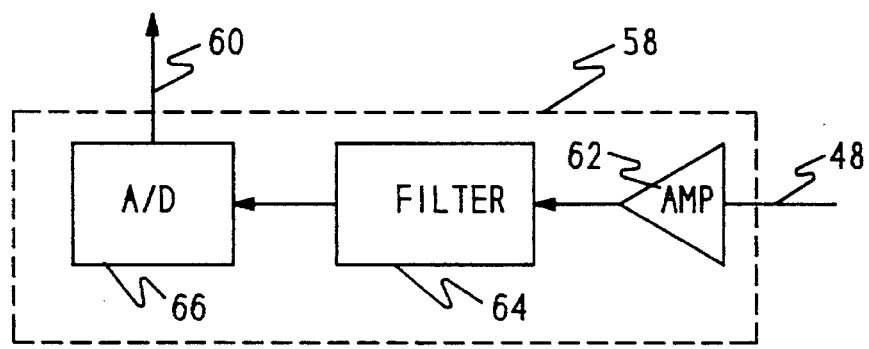
FIG. 2 is a block diagram of the capture sense block of FIG. 1, showing in greater particularity a capture sense signal processing unit.

Referring to FIG. 2, the capture sense signal processor 58 of FIG. 1 is illustrated in greater detail. In a preferred embodiment, signal processor 58 includes a pre-amplifier 62 having an input to which sensed electrical activity signals from the atrium are applied. The input of pre-amplifier 62 is electrically connected via conductor 48 of an endocardial lead to the tip electrode 50 located in the right atrium of the heart. The signal from tip electrode 50 is sensed relative to a second electrode, preferably an external conductive surface of the cardiac stimulator housing, or "can," in a unipolar pacing/sensing configuration. Nevertheless, it should also be understood that the input to pre-amplifier 62 can also be connected to a ring electrode. Alternatively, the input to pre-amplifier 62 can be connected to the tip electrode 50 with the signal being sensed relative to a ring electrode in a bipolar sensing configuration, together with either unipolar or bipolar pacing.

The amplified output signal of pre-amplifier 62 is applied to the input of a following filter stage 64 having filter characteristics calculated to discriminate against frequencies that are characteristic of R-waves originating in the ventricle. Filtering techniques for discriminating against R-waves are well known in the art. The filtered output of filter stage 64 is applied to the input of a following analog to digital converter stage 66 in which the amplified and filtered analog signal is digitized for further processing and analysis by microprocessor 20 in accordance with the method for verifying capture described below.

Figure 3:
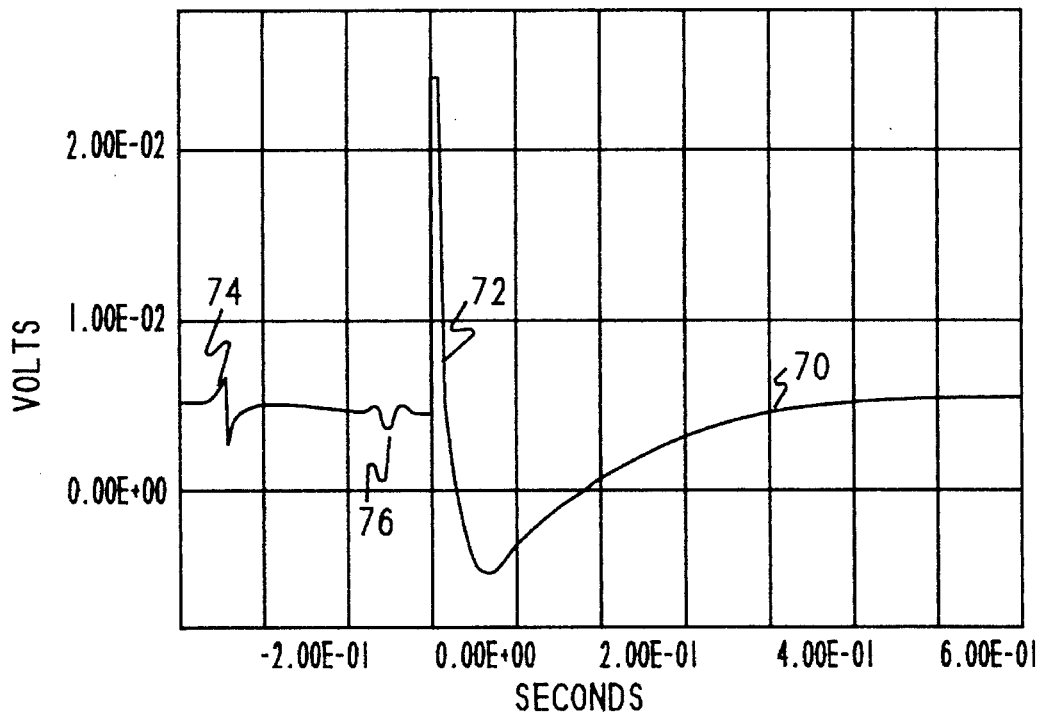
FIG. 3 is an intracardiac atrial electrogram showing an atrial stimulation pulse delivered by unipolar pacing, preceded by an intrinsic atrial depolarization, and showing intrinsic ventricular depolarization as sensed in the atrium.

Referring to FIG. 3, there is illustrated an atrial intracardiac electrogram 70, showing in particular an atrial unipolar stimulus pulse 72, as detected at a tip electrode on a unipolar lead implanted in the atrium. Morphological artifact 74 is an intrinsic P-wave occurring prior to atrial stimulation pulse 72. Morphological artifact 76 is a far-field sensed R-wave originating in the ventricle. Because stimulus pulse 72 occurs within the refractory period following intrinsic P-wave 74, stimulus pulse 72 does not effect atrial capture.

Figure 4:
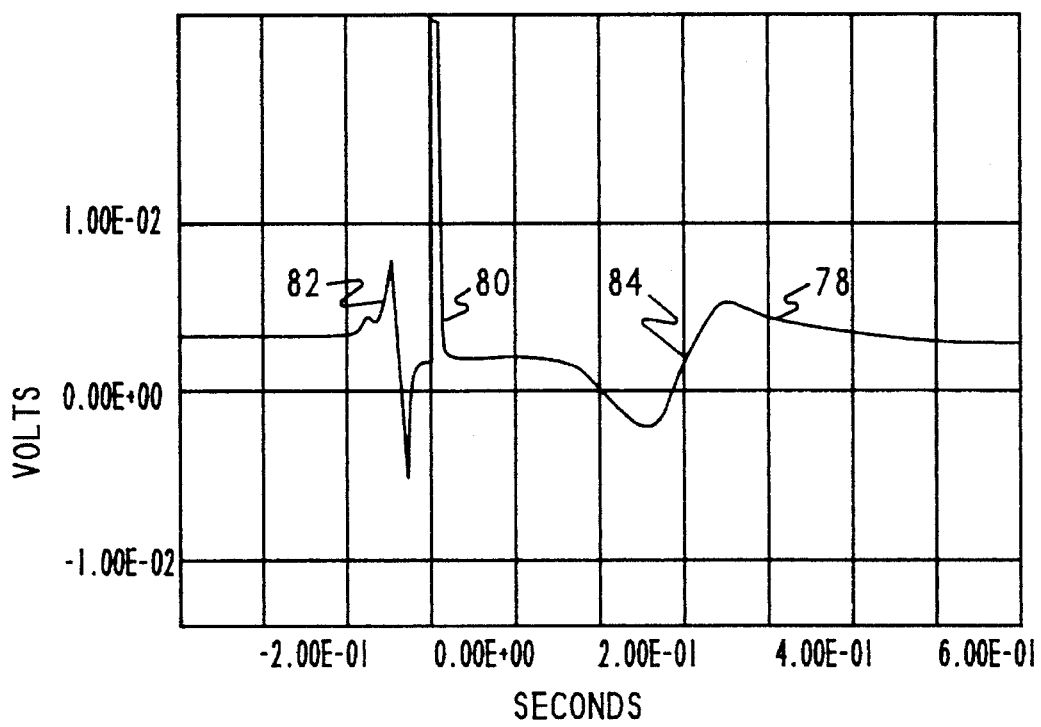
FIG. 4 is an intracardiac ventricular electrogram showing the atrial stimulation pulse of FIG. 3, as sensed in the ventricle, and showing intrinsic ventricular depolarization.

Referring to FIG. 4, there is illustrated a corresponding ventricular intracardiac electrogram 78 as detected at a tip electrode on a unipolar lead implanted in a right ventricle. Morphological artifact 80 is the atrial stimulus pulse of FIG. 3, as sensed by the ventricular electrode. No ventricular stimulus is present. Morphological artifact 82 is a near-field sensed intrinsic ventricular R-wave to which artifact 76 of FIG. 3 corresponds. Morphological feature 84 is the T-wave that follows R-wave 82.

It is evident from FIGS. 3 and 4 that intrinsic ventricular depolarizations may be sensed in the atrium. Such ventricular depolarizations can occur before, during, or after the atrial stimulation pulse and, if not recognized as ventricular R-waves, may be mistaken for P-waves. Hence, it is desirable to discriminate against far-field R-waves as part of any method for analyzing atrial-sensed waveforms to verify atrial capture. One method for discriminating against far-field R-waves is to employ a filter in the atrial capture sense amplifier having characteristics that reject frequencies known to be correlated with R-waves. Such filtering methods are well known in the art. Another method involves detecting the R-wave in the ventricle and blanking out the time interval in which it occurs in the atrial capture sense amplifier. This latter method would require a ventricular electrode, and would be most readily implemented in a dual-chamber pacemaker.

In accordance with the method of the present invention, it is necessary to detect intrinsic atrial depolarizations (P-waves) that precede the atrial stimulus pulse within an interval of time such that the atrial stimulus pulse occurs during the refractory period when the atrium cannot be captured. The importance of sensing the P-wave is described below with reference to FIGS. 5–7. Techniques for sensing P-waves are well-developed in cardiac pacing technology, and will not be discussed further herein.

Figure 5:
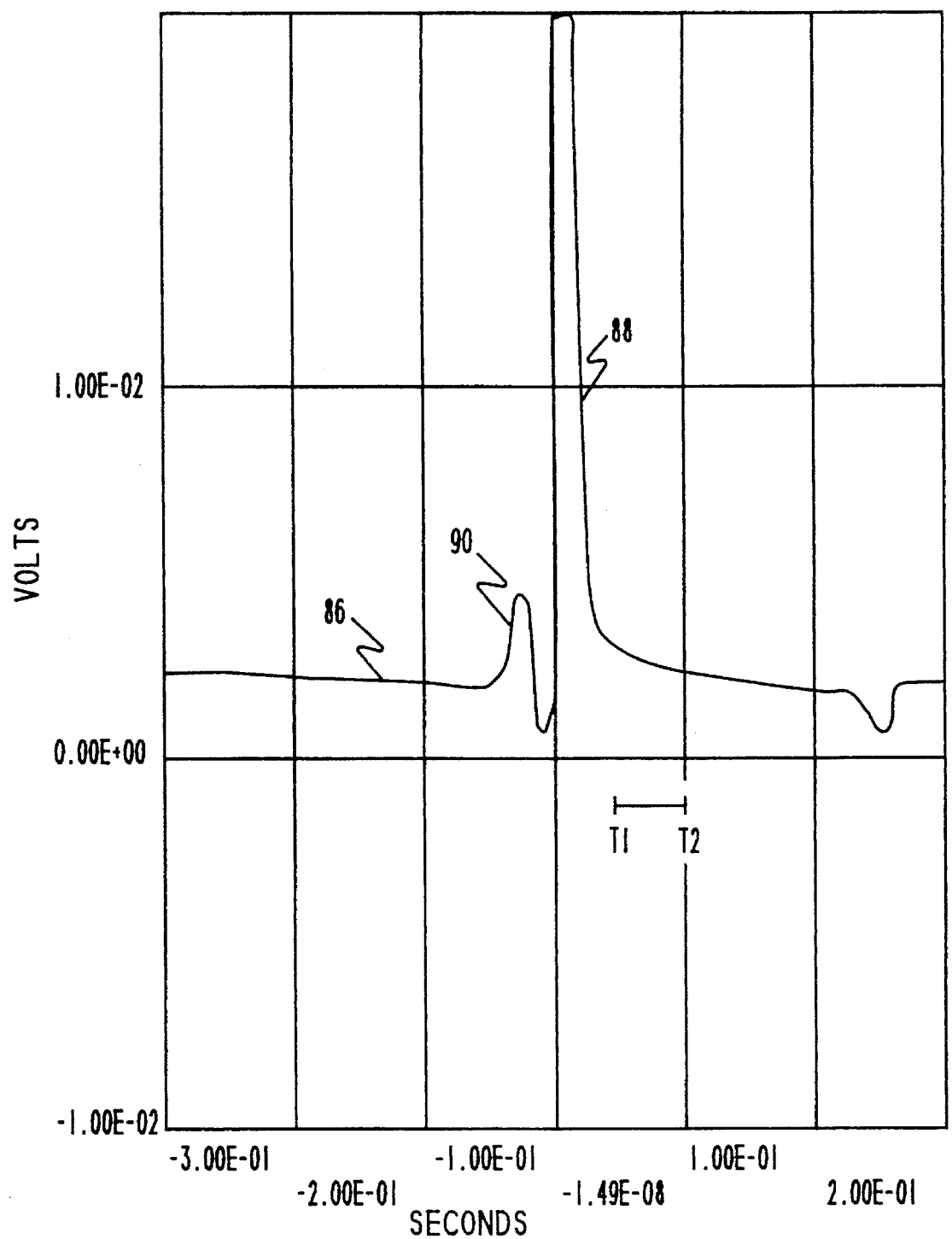
FIG. 5 is an intracardiac atrial electrogram showing a non-capturing atrial stimulation pulse preceded by an intrinsic atrial depolarization.

FIG. 5 shows an atrial electrogram 86 in which an atrial stimulus pulse 88 is preceded by a P-wave 90. Thus, the atrium is in a refractory period at the time of delivery of atrial stimulus pulse 88 and cannot be captured. Electrogram 86 exhibits a post-stimulus morphology having a negative slope during the time interval between times T1 and T2.

Figure 6:
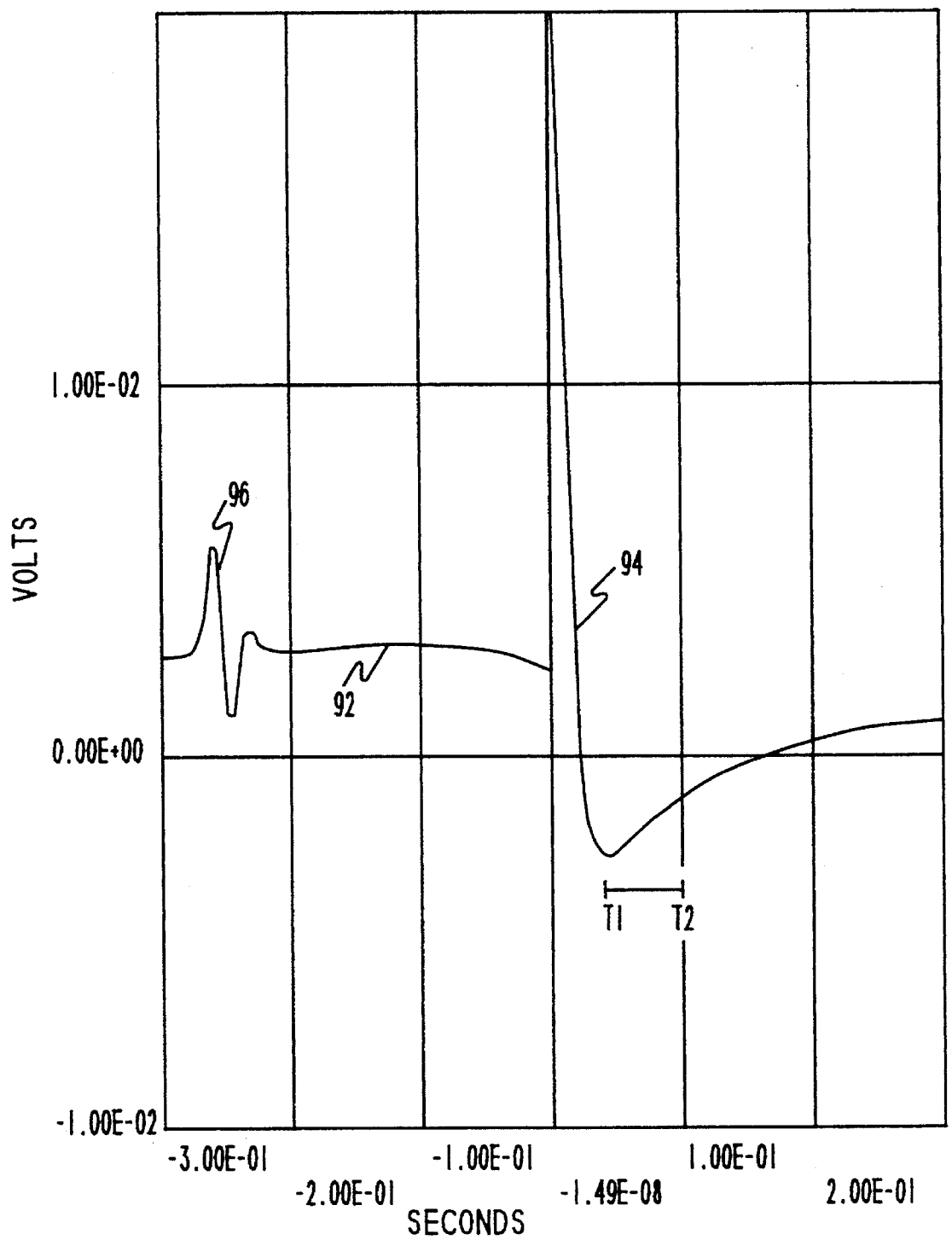
FIG. 6 is another intracardiac atrial electrogram showing a noncapturing atrial stimulation pulse preceded by an intrinsic atrial depolarization.

FIG. 6 shows an atrial electrogram 92 in which an atrial stimulus pulse 94 is preceded by a P-wave 96. As in FIG. 5, the atrium is not captured. Unlike FIG. 5, however, electrogram 92 of FIG. 6 exhibits a post-stimulus morphology having a positive slope during the time interval T1 to T2. Analysis of human electrograms has revealed that the electrograms illustrated in FIGS. 5 and 6 are very typical and that the morphology of the sensed electrograms will conform to those general shapes, differing only in relative amplitudes at T1 and T2.

Figure 7:
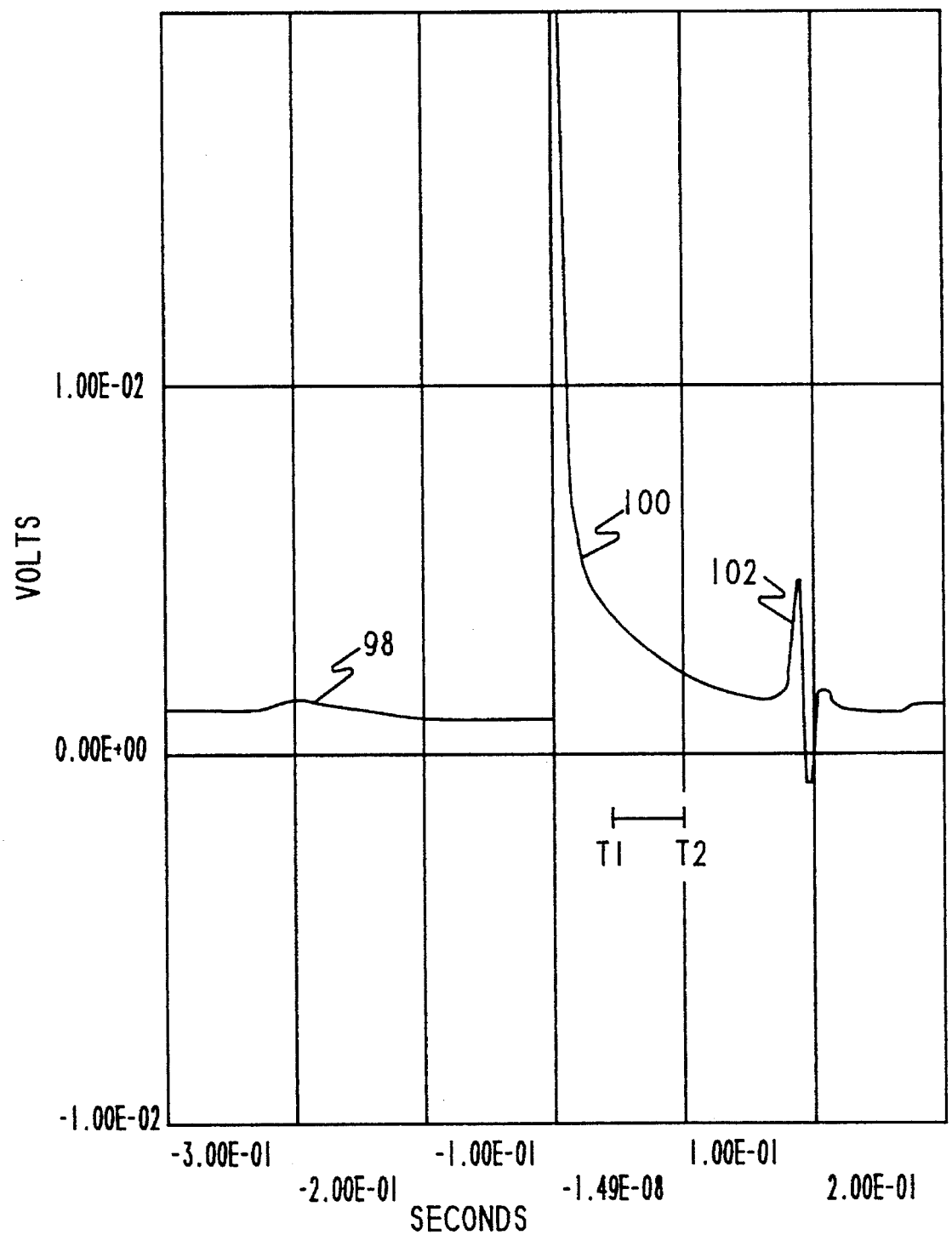
FIG. 7 is an intracardiac atrial electrogram showing a non-capturing atrial stimulation pulse that is not preceded by an intrinsic atrial depolarization, but that is followed by an intrinsic atrial depolarization.

Referring now to FIG. 7, there is shown an atrial electrogram 98 in which an atrial stimulus pulse 100 is not preceded by a P-wave, and yet there is no capture, as indicated by the presence of intrinsic P-wave 102 following stimulus pulse 100. Electrogram 98 exhibits a post-stimulus morphology having a negative slope during the time interval between times T1 and T2.

Analysis of human electrograms has revealed that the post-stimulus morphology illustrated in FIG. 7 is virtually always associated with a non-capture condition, provided that the stimulus pulse is not in the refractory period. The amplitudes at T1 and T2 may be different from that depicted.

Figure 8:
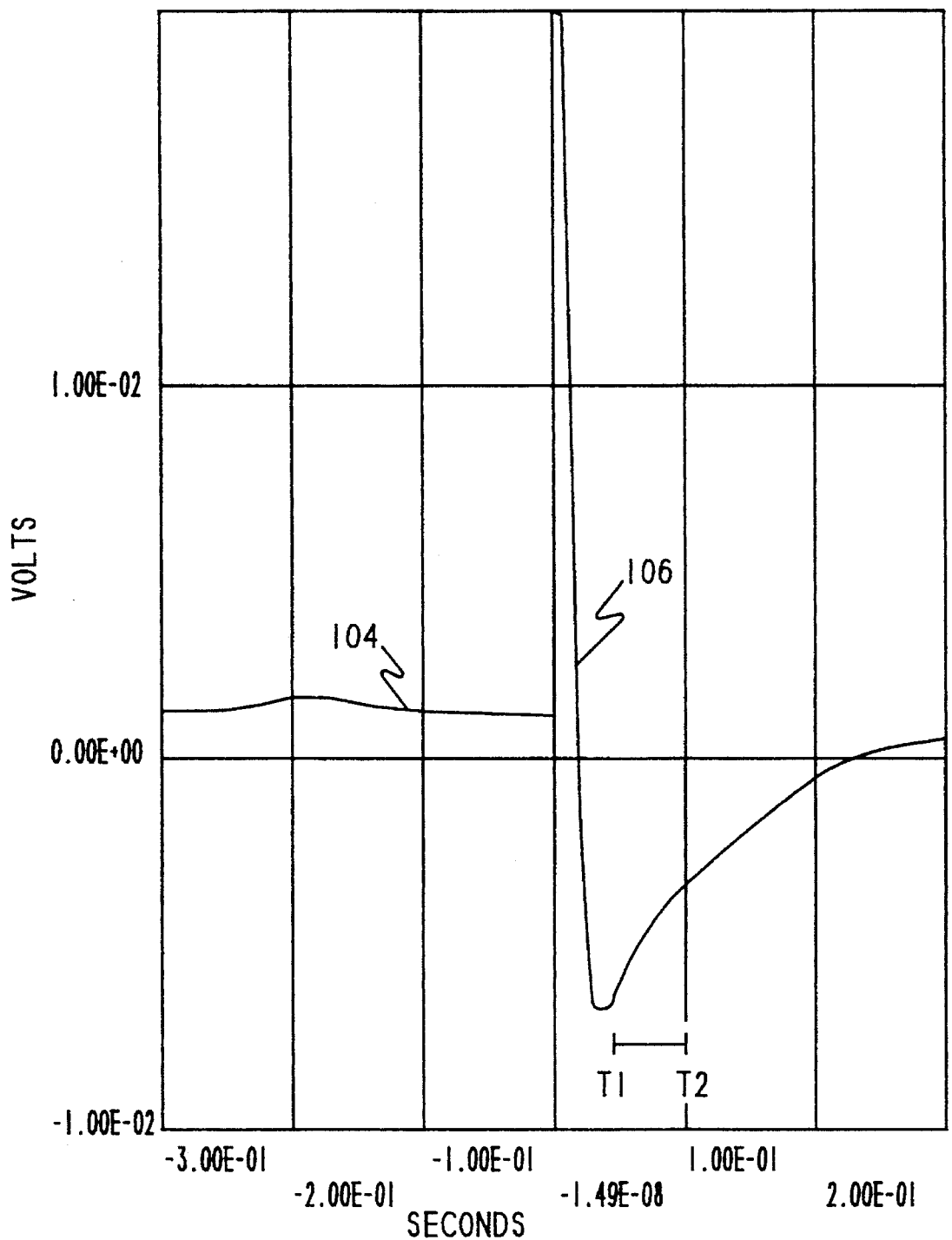
FIG. 8 is an intracardiac atrial electrogram showing a capturing atrial stimulation pulse that is not preceded by an intrinsic atrial depolarization.

Referring now to FIG. 8, there is shown an atrial electrogram 104 in which an atrial stimulus pulse 106, which is not preceded by an intrinsic P-wave, captures the atrium. Electrogram 104 exhibits a positive slope during the post-stimulus time interval between times T1 and T2.

The post-stimulus morphology illustrated in FIG. 8 has been observed through analysis of human electrograms to be virtually always associated with a capture condition, provided that the stimulus pulse is not in the refractory period. The amplitudes at T1 and T2 may differ from those shown. It also has been observed that there is a general correlation between the energy level of the stimulation pulse and the steepness of the slope of the electrogram following the stimulus pulse. The polarity of the slope, i.e., negative versus positive, has been found to be well correlated with capture versus non-capture in those cases where there is no preceding intrinsic P-wave, i.e, where the stimulus pulse is not delivered within the refractory period.

Comparing FIGS. 6 and 8, it can be observed that the electrogram morphologies 92 and 104 are similar and exhibit positive post-stimulus slopes. Yet, FIG. 6 shows a non-capture condition while FIG. 8 shows a capture condition. These two cases can be distinguished in that the non-capture shown in FIG. 6 involves an intrinsic P-wave that precedes the stimulation pulse. It has been observed that there is no reliable correlation between polarity of the slope of the post-stimulus electrogram and capture, where an intrinsic P-wave precedes the stimulation pulse such that the stimulation pulse is delivered during the refractory period. Thus, detection of the post-stimulus electrogram slope is not sufficient to verify capture, as it is indeterminate where there is a preceding P-wave. In the absence of a preceding P-wave, however, the post-stimulus electrogram slope is highly correlated with capture. Since the presence of a preceding P-wave virtually assures that the stimulating pulse will not capture, due to being delivered within the refractory period, detecting whether a preceding P-wave occurred, and detecting the post-stimulus electrogram slope (in at least those cases where there was not a preceding P-wave), provides sufficient information to determine capture status.

To avoid misunderstanding, the definition of "slope" as used above should be made clear. The preferred method of calculating the slope during the interval between times T1 and T2 is to subtract the amplitude at T1 from the amplitude at T2, thus representing the slope of a straight line drawn between the amplitudes at times T1 and T2.

Examination of human electrograms has revealed that a preferred value for T1 is a time 40 msec following the leading edge of the atrial pacing pulse. For T2, values of 70 msec following that leading edge have been found to be adequate in most cases, but the most preferred value is 100 msec. To account for variability among patients, it would be desirable to provide for the values of T1 and T2 to be programmable in a cardiac stimulator in which the present method is implemented.

Figure 9:
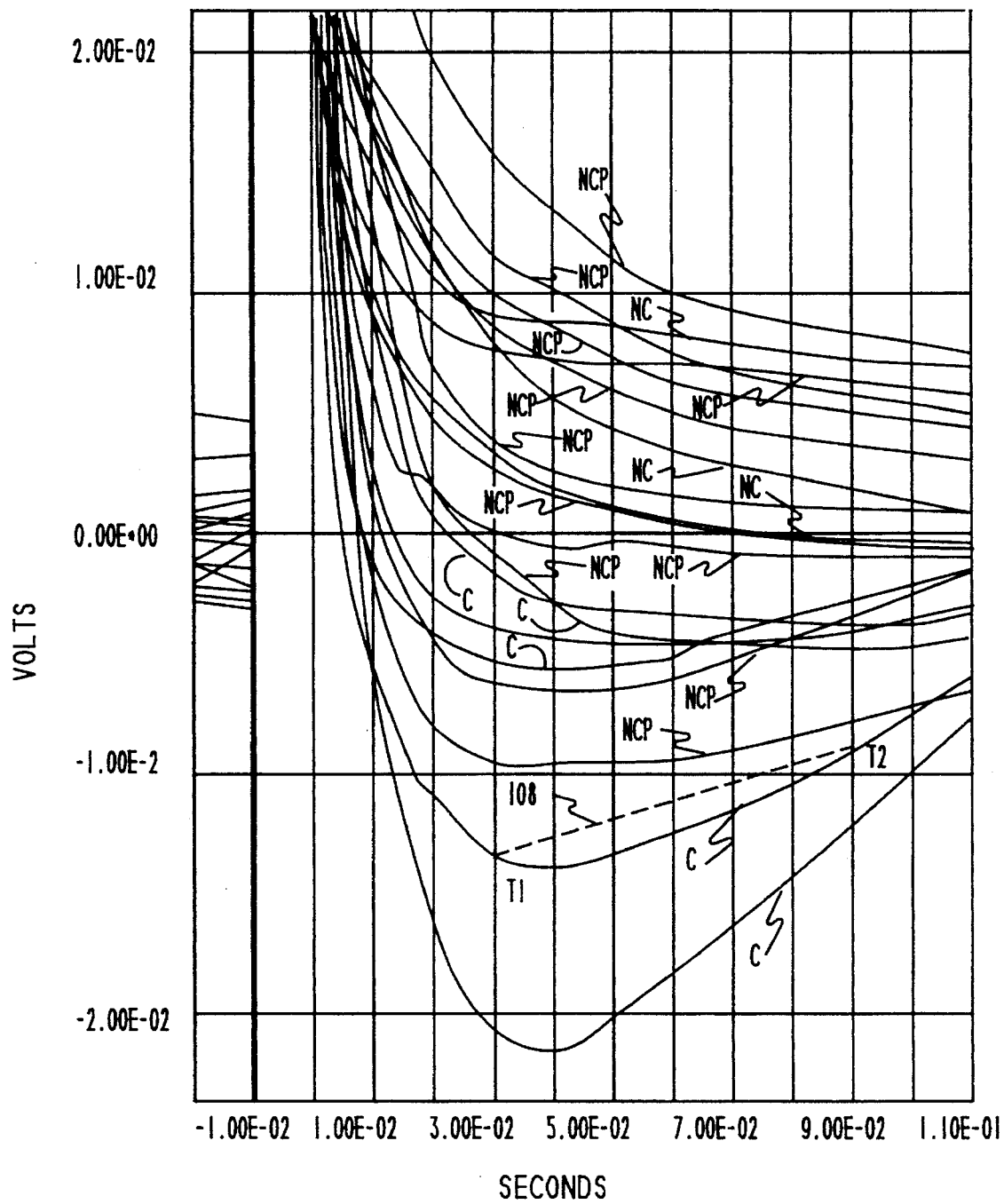
FIG. 9 is an overplot of intracardiac atrial electrograms during a period of time following delivery of an atrial stimulation pulse, some of which electrograms depict capture morphologies and some of which depict non-capture morphologies.

FIG. 9 is an overplot of human atrial electrograms for a chronic implanted atrial lead, resulting from stimulus pulses having various amplitudes and durations. The period of time from 10 msec before delivery of the atrial stimulation pulse to 110 msec after delivery of the atrial stimulation pulse is shown. Each of the electrograms that are labeled NCP represent non-captures that were preceded by an intrinsic P-wave. It can be seen that the class of NCP electrograms includes post-stimulus morphologies having either positive or negative slopes in the time interval between times T1 and T2. Each of the electrograms that are labeled NC represent non-captures that were not preceded by an intrinsic P-wave. It can be seen that the class of NC electrograms includes post-stimulus morphologies having only negative slopes in the time interval between times T1 and T2. Each of the electrograms that are labeled C represent captures that were not preceded by an intrinsic P-wave. It can be seen that the class of C electrograms includes post-stimulus morphologies having only positive slopes in the time interval between times T1 and T2.

The preferred method for determining the slope of the evoked response is illustrated in FIG. 9 for one of the capture electrograms labeled C. Line 108 connects the amplitudes of the example electrogram at times T1 and T2. Since the amplitude at T2 is greater than the amplitude at T1, the slope is deemed to be positive.

It should be recognized that the correlation between positive slope and capture, and between negative slope and non-capture, is dependent upon the relative polarities of the system, and it is to be expected that the correlation would be reversed in a pacing and sensing system having differently arranged polarities. Nevertheless, regardless of the polarity convention adopted, the correlation between post-stimulus morphology and capture status is expected to remain consistent.

It should also be recognized that in this description of the invention, a slope of zero, i.e. horizontal, has been defined as the demarcation between a slope indicative of capture and a slope indicative of non-capture. Within any particular pacing and sensing system, however, it may be necessary to subtract a slope-offset from the measured slope to obtain consistent and accurate verification of capture. In other words, the method employs a comparison of a measured slope with a slope threshold that demarcates capture from non-capture. Thus, where the measured slope surpasses the pre-selected demarcation slope, whatever the value and polarity of the demarcation slope may be, then capture is deemed to have occurred and a signal to that effect is generated.

The present invention has been described with particularity in terms of a preferred method, for implementation in a preferred embodiment of an apparatus, by way of illustration and not limitation. The scope of the invention is defined by the claims appended hereto. Variations of the particular embodiment described herein that incorporate the principles of the present invention may still fall within the scope of the appended claims.

I claim:

1. A method of verifying whether an atrium of a heart has been captured by an electrical cardiac stimulation pulse delivered to the atrium, by sensing a cardiac signal via an electrode located in the atrium, comprising the steps of:

a) sensing a waveform signal at said electrode during a period of time extending from a time preceding the time of delivery of said cardiac stimulation pulse to a time following the time of delivery of said cardiac stimulation pulse;

b) analyzing said sensed waveform-signal by:
detecting whether said sensed waveform signal includes a P-wave component occurring at a time prior to the time of delivery of said cardiac stimulation pulse such that said stimulation pulse would have been delivered within a refractory period of said atrium;
determining the slope of said sensed waveform signal within a selected interval of time beginning at a selected time after the time of delivery of said cardiac stimulation pulse; and c) generating a signal indicative of capture status, where said capture status signal indicates:
capture, if and only if a P-wave component is not detected and the determined slope of said sensed waveform signal surpasses a pre-selected slope threshold demarcating capture from non-capture; or
non-capture, if either:
a P-wave component is detected; or
a P-wave component is not detected and the determined slope of said sensed waveform signal does not surpass a pre-selected slope threshold demarcating capture from non-capture.

2. The method of claim 1 in which the selected interval of time within which the slope of said sensed waveform signal is determined begins at about 40 msec following the time at which said cardiac stimulation pulse was delivered.

3. The method of claim 2, in which the selected interval of time within which the slope of said sensed waveform signal is determined ends at least about 70 msec following the time at which said cardiac stimulation pulse was delivered.

4. The method of claim 3, in which the selected interval of time within which the slope of said sensed waveform signal is determined ends at most about 100 msec following the time at which said cardiac stimulation pulse was delivered.

5. The method of claim 1 in which said sensing step further includes:
discriminating against far-field R-wave components of said sensed waveform signal.

6. The method of claim 2, in which said sensing step further includes:
discriminating against far-field R-wave components of said sensed waveform signal.

7. The method of claim 3, in which said sensing step further includes:
discriminating against far-field R-wave components of said sensed waveform signal.

8. The method of claim 4, in which said sensing step further includes:
discriminating against far-field R-wave components of said sensed waveform signal.

9. A method of verifying whether an atrium of a heart has been captured by an electrical cardiac stimulation pulse delivered to the atrium, by sensing a cardiac signal via an electrode located in the atrium, comprising the steps of:

a) sensing a waveform signal at said electrode during a period of time extending from a time preceding the time of delivery of said cardiac stimulation pulse to a time following the time of delivery of said cardiac stimulation pulse;

b) analyzing said sensed waveform signal by:
detecting whether said sensed waveform signal includes a P-wave component occurring at a time prior to the time of delivery of said cardiac stimulation pulse such that said stimulation pulse would have been delivered within a refractory period of said atrium, and, if and only if a P-wave is not detected, determining the slope of said sensed waveform signal within a selected interval of time beginning at a selected time after the time of delivery of said cardiac stimulation pulse; and c) generating a signal indicative of capture status, where said capture status signal indicates:
non-capture, if a P-wave component is detected; or
capture, if a P-wave component is not detected and the determined slope of said sensed waveform signal surpasses a pre-selected slope threshold demarcating capture from non-capture.

10. The method of claim 9, in which the selected interval of time within which the slope of said sensed waveform signal is determined begins at about 40 msec following the time at which said cardiac stimulation pulse was delivered.

11. The method of claim 10, in which the selected interval of time within which the slope of said sensed waveform signal is determined ends at least about 70 msec following the time at which said cardiac stimulation pulse was delivered.

12. The method of claim 11, in which the selected interval of time within which the slope of said sensed waveform signal is determined ends at most about 100 msec following the time at which said cardiac stimulation pulse was delivered.

13. The method of claim 9, in which said sensing step further includes:

discriminating against far-field R-wave components of said sensed waveform signal.

14. The method of claim 10, in which said sensing step further includes:

discriminating against far-field R-wave components of said sensed waveform signal.

15. The method of claim 11, in which said sensing step further includes:

discriminating against far-field R-wave components of said sensed waveform signal.

16. The method of claim 12, in which said sensing step further includes:

discriminating against far-field R-wave components of said sensed waveform signal.

* * * * *